(12) United States Patent
Karlsson

(10) Patent No.: US 9,125,988 B2
(45) Date of Patent: Sep. 8, 2015

(54) MEDICAMENT DELIVERY DEVICE

(75) Inventor: Anders Karlsson, Saltsjö-Boo (SE)

(73) Assignee: SHL Group AB, Nacka Strand (SE)

( * ) Notice: Subject to any disclaimer, the term of this patent is extended or adjusted under 35 U.S.C. 154(b) by 291 days.

(21) Appl. No.: 13/696,368

(22) PCT Filed: Apr. 27, 2011

(86) PCT No.: PCT/SE2011/050508
§ 371 (c)(1),
(2), (4) Date: Nov. 6, 2012

(87) PCT Pub. No.: WO2011/139212
PCT Pub. Date: Nov. 10, 2011

(65) Prior Publication Data
US 2013/0053790 A1  Feb. 28, 2013

Related U.S. Application Data

(60) Provisional application No. 61/332,255, filed on May 7, 2010.

(30) Foreign Application Priority Data

May 7, 2010 (SE) ........................................ 1050453

(51) Int. Cl.
*A61M 5/315* (2006.01)
*A61M 5/20* (2006.01)
*A61M 5/32* (2006.01)

(52) U.S. Cl.
CPC ...... *A61M 5/2033* (2013.01); *A61M 2005/2013* (2013.01); *A61M 2005/2073* (2013.01); *A61M 2005/3247* (2013.01)

(58) Field of Classification Search
CPC .................. A61M 5/2033; A61M 2005/3247; A61M 2005/2073

USPC ............................................ 604/218, 48, 187
See application file for complete search history.

(56) References Cited

U.S. PATENT DOCUMENTS

| 4,755,172 A | 7/1988 | Baldwin |
| 5,478,316 A | 12/1995 | Bitdinger et al. |

(Continued)

FOREIGN PATENT DOCUMENTS

| WO | 98/30811 A1 | 7/1998 |
| WO | 2010/018411 A1 | 2/2010 |

OTHER PUBLICATIONS

Swedish Patent Office, Int'l Search Report in PCT/SE2011/050508, Aug. 18, 2011.

(Continued)

*Primary Examiner* — Edelmira Bosques
(74) *Attorney, Agent, or Firm* — Piedmont Intellectual Property

(57) ABSTRACT

A medicament delivery device has a housing for a medicament container and a drive unit for a stopper in the container to expel a dose of medicament, the drive unit having a plunger rod and a dual back-to-back force spring assembly connected to the plunger rod; and a lock and release mechanism connected to the drive unit that has a hold member connected to the plunger rod, a rotator member connected to the hold member, and a tubular actuation member linearly slidable in relation to the housing and connected to the rotator member. The hold member is attached to the housing and has a generally tubular lock tube through which the plunger rod extends and two half-cylindrical seats for the dual back-to-back force spring assembly. The lock tube has a resilient lock and release device to interact with both the plunger rod and the rotator member.

15 Claims, 4 Drawing Sheets

(56) References Cited

U.S. PATENT DOCUMENTS 7,470,253 B2 * 12/2008 Kriesel et al. ................ 604/134
2006/0186143 A1 8/2006 Argentine

OTHER PUBLICATIONS

Swedish Patent Office, Written Opinion in PCT/SE2011/050508, Aug. 18, 2011.

* cited by examiner

MEDICAMENT DELIVERY DEVICE

TECHNICAL FIELD

The present invention relates to a medicament delivery device and in particular a device capable of providing certain force characteristics from a drive unit for delivering a dose of medicament.

BACKGROUND OF THE INVENTION

Many medicament delivery devices have an automatic dose delivery function that often consists of drive springs that are capable of acting on movable stoppers arranged inside medicament containers for expelling a dose of medicament through a medicament delivery member such as e.g. an injection needle.

The automatic delivery mechanism in a medicament delivery device often includes a compressed helical drive spring acting on a plunger rod to urge it in the proximal direction of the device upon activation. A compressed compression spring provides a force that is large enough to overcome the so called break loose force of the stopper, i.e. release the stopper from the inner wall of the medicament container, and the spring at its full extension, which usually is not the full decompression, provides a force that is large enough to complete the dose delivery but also can cause a breakage of the glass medicament container.

In order to handle this, some devices utilize so called constant force springs which are coil springs of strip material which have been shaped and pre-tensioned into tightly wound rolls. The spring is used in a linear movement, e.g. moving a plunger rod in the proximal direction, and produces almost constant force throughout its deflection. Document U.S. Pat. No. 5,478,316 discloses a medicament delivery device utilizing such a spring for driving a plunger rod during dose delivery. Further, it is sometimes desirable to have different force levels during different operations such as e.g. penetration and subsequent injection, but constant force during each operation.

Document EP 0 953 122 discloses such a spring. Although this type of springs is better in many aspects than the compression springs, they still have drawbacks. One such drawback is that the load on a plunger rod is non-symmetrical due to that the spring runs on the side of and parallel with the plunger rod, whereby a bending force is exerted on the plunger rod. The bending force could cause a breaking of the plunger rod or a deflection of the plunger rod such that it comes in contact with other components of the device, leading to increased friction or even jamming of the plunger rod.

A solution to these problems is known from document US 200610186143A1 wherein the load on the plunger rod is symmetrical. However, there is still rum for improvements wherein the device can be constructed with a few number of components where each component can achieve different functions.

BRIEF DESCRIPTION OF THE INVENTION

The aim of the present invention is to utilize the advantages with the coiled strip spring but avoiding the drawbacks of the known devices utilizing such springs.

This aim is obtained by the features of the independent patent claim. A preferable embodiment of the present invention is set forth in the dependent patent claims.

According to a main aspect of the invention it is characterised by a medicament delivery device comprising a housing, which housing is arranged to accommodate a medicament container; a drive unit arranged in said housing and capable of acting on a movable stopper positioned inside said medicament container for expelling a dose of medicament, wherein said drive unit comprises an elongated plunger rod and a dual back-to-back force spring assembly operatively connected to said plunger rod such as to provide a symmetrical load on said plunger rod; a locking and release mechanism operatively connected to said drive unit and capable of releasing said drive unit upon activation, wherein the locking and release mechanism comprises a hold member operatively connected to the plunger rod, a rotator member operatively connected to the hold member, and a tubular actuation member linearly slidable in relation to the housing and operatively connected to the rotator member; wherein the hold member is fixedly attached to the housing and comprises a generally tubular lock tube through which the plunger rod extends and two seats designed as half-cylinders open towards the proximal direction for housing the dual back-to-back force spring assembly, and wherein the lock tube comprises resilient locking and release means configured to interact with both the plunger rod and the rotator member.

According to yet a further aspect of the invention, the dual back-to-strip material having a front side surface and a back side surface and which strip material is shaped and pre-tensioned into a tightly wound roll with an outer end, and wherein each wound roll is cradled in a corresponding seat of the hold member and each outer end having their back side surfaces towards each other is attached to each side of a transversal post which is attached to the distal end of the plunger rod.

According to yet another aspect of the invention, the elongated plunger rod is arranged with a plurality of recesses on its outer circumference surface, and wherein said recesses are arranged in rows along the longitudinal direction.

According to another aspect of the invention, the plunger rod and the spring assembly are arranged to be moved between a loaded state in which a proximal end of the plunger rod is abutting the stopper positioned at a distal end within the medicament container and in which a portion of the strip material is unrolled and extends parallel on each side of the plunger rod and a relaxed state in which the plunger rod is abutting the stopper positioned at a proximal end within the medicament container and in which the strip material is rolled up.

According to yet another aspect of the invention, the rotator member comprises an inner circumferential surface having inner ledges and inner grooves, and an outer circumferential surface having a number of outer guides forming two paths on opposite sides of the rotator member.

According to a further aspect of the invention, the rotator member is arranged to be rotated from a locked position in which the interaction between the first radial outwardly directed protrusions and the ledges forces the radial flexible tongues radial inwards such that the first radial inwardly directed protrusions are engaged into the recesses of the plunger rod for holding the plunger rod and the spring assembly in the loaded state, and a released position in which the interaction between the first radial outwardly directed protrusions and the inner grooves on the inner surface of the rotator member forces the radial flexible tongues radial outwards such that the first radial inwardly directed protrusions are disengaged from the recesses of the plunger rod for releasing the plunger rod and the spring assembly from the loaded state.

According to yet a further aspect of the invention, the tubular actuation member comprises a proximal generally tubular part protruding through the proximal end of the housing, and two longitudinally extending arms wherein each of the longitudinally extending arms comprises a second radial inwardly directly protrusion arranged to interact into the paths on the outer surface of the rotator member, such that when proximal generally tubular part is pressed against a drug delivery site, said actuation member is linearly and distally displaced forcing the rotator to rotate from the locked position to the released position.

According to another aspect of the invention, the device further comprises a security locking member extending through a distal end of said housing and having a proximal end operatively connected to said actuation member, wherein said security locking member is movable between a first position in which the security locking member is locked to said actuation member for preventing the actuation member to be linearly and distally displaced when the actuation member is pressed against the drug delivery site, and a second position in which the security locking member is unlocked from said actuation member for allowing the actuation member to be linearly and distally displaced when the actuation member is pressed against the drug delivery site.

There are several advantages with the present invention. Because of the use of a dual back to back spring assembly acting on the plunger rod, a symmetrical load is obtained on the plunger rod, i.e. there is no bending or offset force acting on the plunger rod as with a single spring. Thus, the advantageous properties and characteristics of springs of strip material as mentioned above is maintained but without the drawbacks of non-symmetrical load.

Moreover, the use of a holding member to control the holding and releasing of the drive means and to house the spring mechanism is advantageous because several functions can be implemented on the holding member.

Further the use of a rotator to control the function and action of the device is also advantageous because several functions can be implemented on the inner and outer surface of the rotator. This means that several actuation and release mechanisms are controlled by the rotator and its configuration. Thus, the rotator, the holding member and the drive means form a power pack with a few components that can be easily mounted within the housing.

Thus an actuation member may be placed at the proximal end of the device, which triggers a dose delivery when pressed against the delivery site. This may thus comprise a needle guard that extends somewhat out of the housing and surrounds an injection needle.

In order to provide a higher degree of safety the actuation member may be locked by a safety locking member such that the actuation member cannot initiate an activation of the device unless the locking member has been operated. This ascertains that an activation of the device cannot be unintentionally started by merely pressing on the actuation member.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

Figure 2:
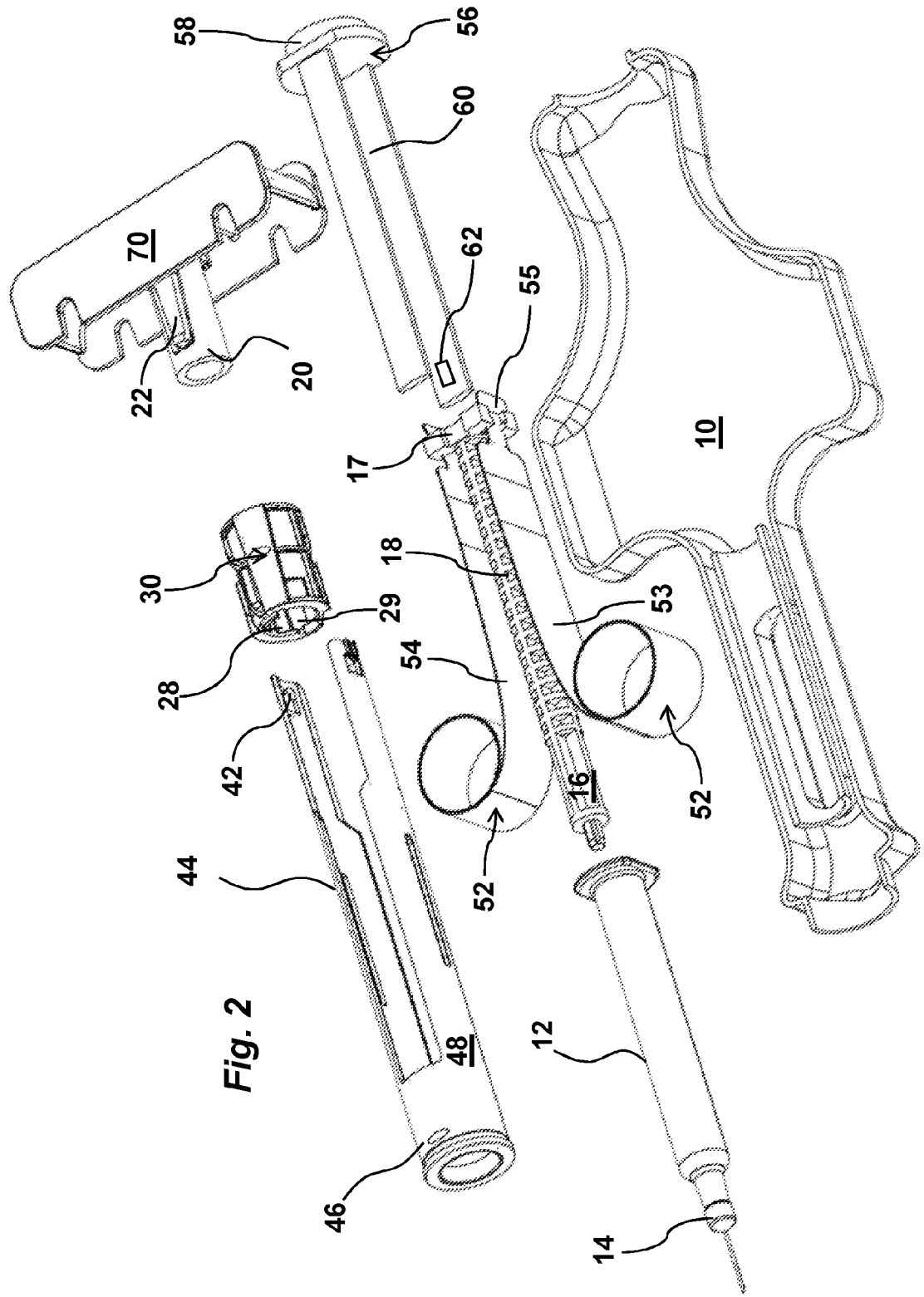
FIG. 2 shows an exploded view of the device of FIG. 1.

The present invention relates to a medicament delivery device comprising a housing arranged to accommodate a medicament container, a drive unit arranged in said housing and capable of acting on a movable stopper positioned inside said medicament container for expelling a dose of medicament, a locking and release mechanism operatively connected to said drive unit and capable of releasing said drive unit upon activation, wherein said drive unit comprises an elongated plunger rod and a dual back-to-back force spring assembly operatively connected to said plunger rod such as to provide a symmetrical load on said plunger rod In the present application, the wording dual back-to-back force spring assembly is defined as an assembly comprising two springs of strip material having a front surface and a back surface and which strip material is shaped and pre-tensioned into a tightly wound roll with an outer end, and wherein each wound roll is cradled in a seat which is secured to the housing and each outer end having their back side surfaces towards each other is attached to each side of a transversal post which is attached to the distal end of the plunger rod, as seen in FIG. 2. It must be observed that the springs of strip material can be a constant-force spring which is a spring for which the force it exerts over its range of motion is an almost constant force or a variable force spring which is a spring that delivers dependable variable force to precisely match increasing or decreasing force requirements.

Figure 1:
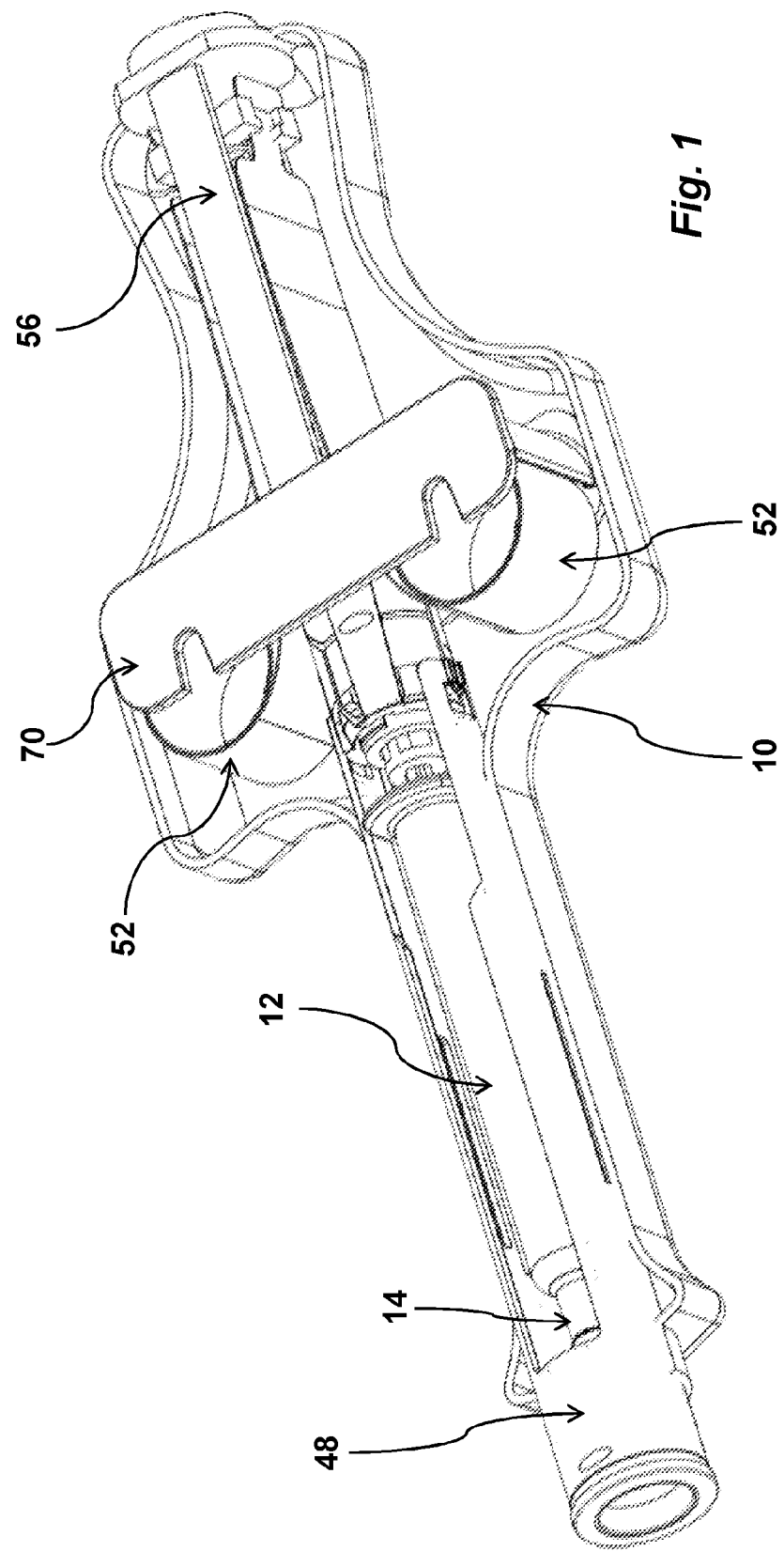
FIG. 1 shows a perspective view of a medicament delivery device with a housing part removed for clarity.

The medicament delivery device shown in the drawings is an exemplary embodiment. As seen in FIG. 1, the housing 10 comprises a proximal part arranged to accommodate the medicament container 12 which is arranged with a medicament delivery member 14 at its proximal end. In the shown exemplary embodiment, the medicament delivery member 14 is an injection needle but it is to be understood that other types of medicament delivery members may also be used, such as mouth or nose pieces, nozzles, nebulizers. It is also to be understood that the medicament container could be a cartridge having attachment means for attaching a medicament delivery member.

In the exemplary embodiment, the elongated plunger rod 16 is arranged in the housing 10 with a proximal end in contact with a movable stopper (not shown) inside said medicament container 12. The plunger rod 16 is arranged with a plurality of recesses 18 on its outer circumference surface, and wherein said recesses are arranged in rows along the longitudinal direction.

In the exemplary embodiment, the locking and release mechanism comprises a hold member 70 fixedly attached to the housing and operatively connected to the plunger rod, a rotator member 30 operatively connected to the hold member, and a tubular actuation member 48 linearly slidable in relation to the housing and operatively connected to the rotator member, as will be explained below.

Figure 3:
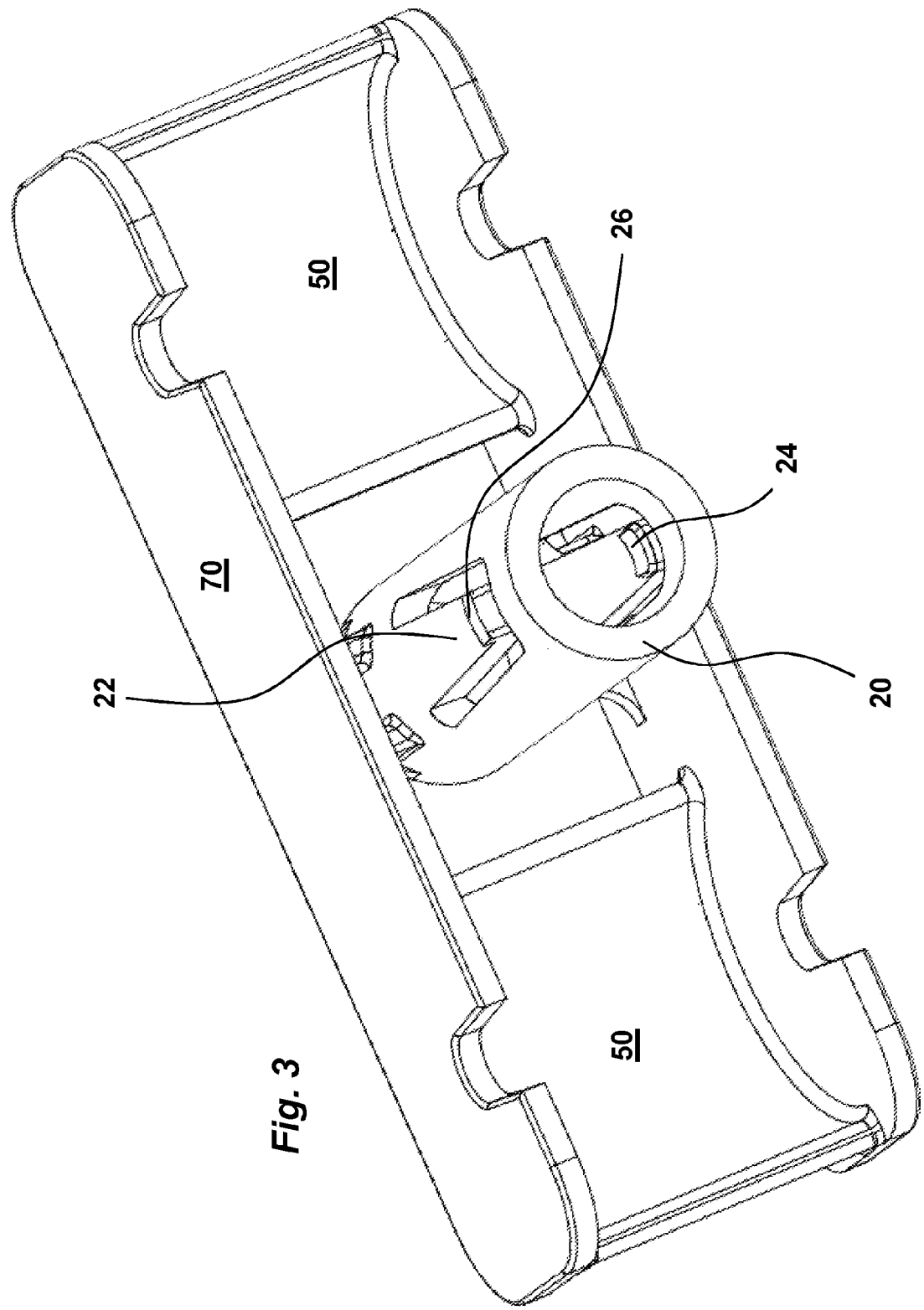
FIG. 3 shows a detailed view of a component comprised in the device of FIG. 1.

In the exemplary embodiment, the hold member 70 comprises a generally tubular lock tube 20 through which the plunger rod 16 extends and two seats 50 designed as half-cylinders open towards the proximal direction for housing the dual back-to-back force spring assembly. The lock tube 20 comprises resilient locking and release means configured to interact with both the plunger rod and the rotator member. The resilient locking and release means being in the exemplary embodiment two oppositely positioned radial flexible tongues 22, FIG. 3, where each tongue 22 is arranged with a first radial inwardly directed protrusion 24 and with a first radial outwardly directed protrusion 26.

In the exemplary embodiment, the dual back-to-back force spring assembly comprises two springs 52 of strip material having a front side surface 53 and a back side surface 54 and which strip material is shaped and pre-tensioned into a tightly wound roll with an outer end 55, and wherein each wound roll is cradled in a corresponding seat 50 of the hold member and each outer end having their back side surfaces towards each other is attached to each side of a transversal post 17 which is attached to the distal end of the plunger rod. Further, the plunger rod and the spring assembly are arranged to be moved between a loaded state in which a proximal end of the plunger rod is abutting the stopper positioned at a distal end within the medicament container and in which a portion of the strip material is unrolled and extends parallel on each side of the plunger rod and a relaxed state in which the plunger rod is abutting the stopper positioned at a proximal end within the medicament container and in which the strip material is rolled up. Since each outer end of the springs, having their back side surfaces towards each other, is attached to each side of the transversal post 17, a symmetrical load on said plunger rod is provided when the plunger rod and the spring assembly are moved from the loaded state to the relaxed state.

Figure 4:
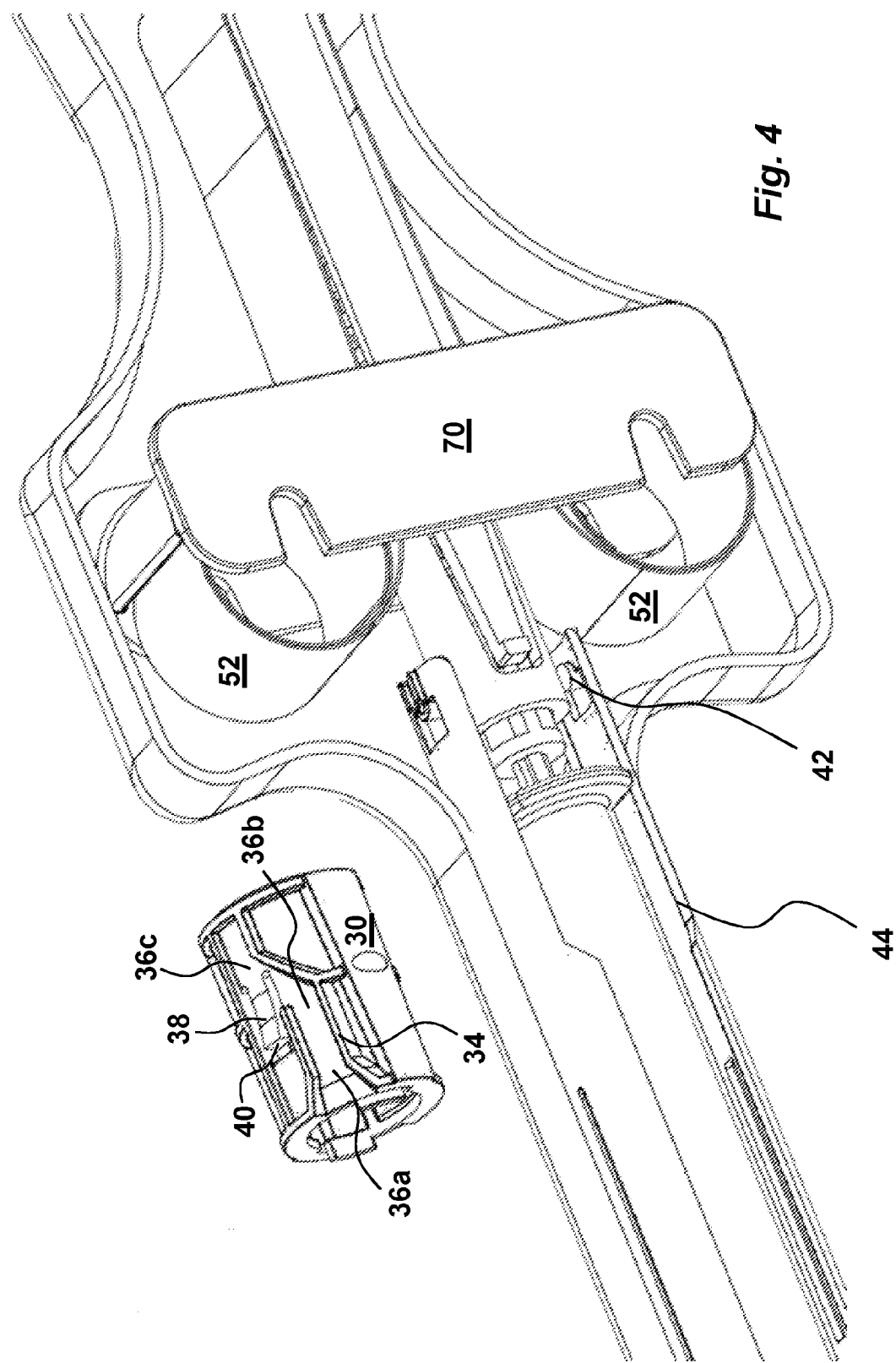
FIG. 4 shows another detailed view of the device of FIG. 1.

In the exemplary embodiment, the rotator member 30 comprises an inner circumferential surface having inner ledges 28 and inner grooves 29, and an outer circumferential surface having a number of guides 34 forming two paths 36 on opposite sides of the rotator member. As seen in FIG. 4 each path comprises a first longitudinally directed path section 36*a*, followed by a second inclined path section 36*b*, which in turn is followed by a third longitudinally directed path 36*c*. At the proximal end of the third longitudinal path, a flexible tongue 38 is further arranged, directed in the proximal direction, which tongue 38 is arranged with a wedge-shape so as to form proximally directed end surfaces 40. Further, the rotator member is arranged to be rotated from a locked position in which the interaction between the first radial outwardly directed protrusions 26 and the inner ledges 28 forces the radial flexible tongues 22 radial inwards such that the first radial inwardly directed protrusions 24 are engaged into the recesses 18 of the plunger rod 16 for holding the plunger rod and the spring assembly in the loaded state, and a released position in which the interaction between the first radial outwardly directed protrusions 26 and the inner grooves 29 on the inner surface of the rotator member forces the radial flexible tongues 22 radial outwards such that the first radial inwardly directed protrusions 24 are disengaged from the recesses (18) of the plunger rod 16 for releasing the plunger rod and the spring assembly from the loaded state.

In the exemplary embodiment, the tubular actuation member 48 comprises a proximal generally tubular part 46 protruding through the proximal end of the housing a certain distance, and two longitudinally extending arms 44 wherein each of the longitudinally extending arms 44 comprises a second radial inwardly directed protrusion 42 arranged to interact into the paths 36 on the outer surface of the rotator member, such that when proximal generally tubular part 46 is pressed against a drug delivery site, said actuation member is linearly and distally displaced forcing the rotator to rotate from the locked position to the released position. Further an actuation member spring (not shown) is arranged between the actuation member 48 and the housing 10 for urging the actuation member 48 in the proximal direction.

The device is also provided with a security locking member 56. The security locking member 56 extends through a distal end of said housing and has a proximal end operatively connected to said actuation member, wherein said security locking member is movable between a first position in which the security locking member is locked to said actuation member for preventing the actuation member to be linearly and distally displaced when the actuation member is pressed against the drug delivery site, and a second position in which the security locking member is unlocked from said actuation member for allowing the actuation member to be linearly and distally displaced when the actuation member is pressed against the drug delivery site.

In the exemplary embodiment, the locking member 56 comprises an activation button 58 having a distal end protruding through a passage at the distal end of the housing and two longitudinally and proximally extending arms 60, wherein each arm comprises at its proximal end a third radial inwardly directed protrusion 62 arranged to co-act with the distal end surface of each longitudinally extending arm 44 of the actuation member 48.

The device is intended to function as follows. When the device is delivered to the user, a medicament container 12 provided with a medicament delivery member 14 is preferably placed in the housing and the actuation member 48 surrounds the medicament delivery member.

When a dose of medicament is to be delivered to the user, the proximal generally tubular part 46 of the actuation member 48 is pressed against a delivery site, such as e.g. an injection site. However the actuation member 48 is prevented from being distally moved into the housing because the distal end surfaces of each longitudinally extending arm 44 of the actuation member 48 are abutting the corresponding third radial inwardly directed protrusions 62 of the security locking member.

The user thus first has to rotate the activation button 58 of the locking member 56 whereby the third radial inwardly directed protrusions 62 move out of contact with the distal end surfaces of each longitudinally extending arm 44 of the actuation member 48. When now the proximal generally tubular part 46 of the actuation member 48 is pressed against the delivery site, the second radial inwardly directed protrusions 42 can act on the inclined path section 36*b* and the rotator member 30 is then rotated such an angular distance that the inner ledges 28 are moved out of contact with the first radial outwardly directed protrusions 26 of the flexible tongues 22 of the lock tube 20. The first radial outwardly directed protrusions 26 are then moved into the inner grooves 29 such that the flexible tongues 22 are free to move radial outwards allowing the first radial inwardly directed protrusions 24 to be disengaged from the recesses 18 of the plunger rod 16 and due to the force exerted from the dual back-to-back spring assembly, the plunger rod 16 is urged in the proximal direction, which movement is indicated by a sound of the first radial inwardly directed protrusions 24 when they slide over the recesses 18, and which movement causes the stopper of the medicament container 12 to move in the proximal direction whereby a dose of medicament is expelled through the medicament delivery member 14.

When the dose has been delivered, which is indicated by the end of the sound from the tongues 22, the device is removed from the dose delivery site, whereby the actuation member 48 is urged in the proximal direction by the actuation member spring. The proximal movement of the actuation member 48 causes the second radial inwardly directed protrusions 42 to slide over the wedge-shape of the tongues 38 of the rotator member 30 until the second radial inwardly directed protrusions 42 pass the proximal end surface 40 and the actuation member 48 surrounds the dose delivery member 14. Thereby the actuation member 48 is locked from being moved again in the distal direction and the dose delivery member 14 is protected such that persons handling the device cannot be injured by e.g. unintentional needle sticks when the medicament delivery member is an injection needle.

In the exemplary embodiment the medicament delivery device is a disposable auto-injection device, wherein the meaning of a disposable auto-injector is a non-rechargeable spring-loaded device configured to deliver a single dose of medicament enclosed in a syringe and wherein the meaning of syringe is a medicament container having a needle as delivery member.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
   a housing configured for a medicament container;
   a drive unit in the housing and configured for acting on a movable stopper in the medicament container for expelling a dose of medicament, wherein the drive unit includes an elongated plunger rod and a dual back-to-back force spring assembly operatively connected to the plunger rod so as to provide a symmetrical load on the plunger rod; and
   a lock and release mechanism operatively connected to the drive unit and configured for releasing the drive unit upon activation, wherein the lock and release mechanism includes a hold member operatively connected to the plunger rod, a rotator member operatively connected to the hold member, and a tubular actuation member linearly slidable in relation to the housing and operatively connected to the rotator member;
   wherein the hold member is fixedly attached to the housing and includes a generally tubular lock tube through which the plunger rod extends and two half-cylindrical seats open toward a proximal direction for housing the dual back-to-back force spring assembly; the lock tube includes a resilient lock and release device configured to interact with both the plunger rod and the rotator member; and the resilient lock and release device includes two oppositely positioned radial flexible tongues, each with a first radial inwardly directed protrusion and with a first radial outwardly directed protrusion.

2. The medicament delivery device of claim 1, wherein the plunger rod and spring assembly are movable between a loaded state, in which a proximal end of the plunger rod abuts the stopper positioned at a distal end in the medicament container and in which a portion of the strip material is unrolled and extends parallel on each side of the plunger rod, and a relaxed state, in which the plunger rod abuts the stopper positioned at a proximal end in the medicament container and in which the strip material is rolled up.

3. The medicament delivery device of claim 2, wherein the rotator member has an inner circumferential surface having inner ledges and inner grooves and an outer circumferential surface having a number of outer guides in two paths on opposite sides of the rotator member.

4. The medicament delivery device of claim 3, wherein the rotator member rotates between a locked position, in which the first radial outwardly directed protrusions interact with the ledges thereby forcing the radial flexible tongues radially inward such that the first radial inwardly directed protrusions engage into the recesses of the plunger rod for holding the plunger rod and spring assembly in the loaded state, and a released position, in which the first radial outwardly directed protrusions interact with the inner grooves on the inner surface of the rotator member thereby forcing the radial flexible tongues radially outward such that the first radial inwardly directed protrusions disengage from the recesses of the plunger rod for releasing the plunger rod and the spring assembly from the loaded state.

5. The medicament delivery device of claim 4, wherein the tubular actuation member comprises a proximal generally tubular part protruding through the proximal end of the housing, and two longitudinally extending arms; each longitudinally extending arm comprises a second radial inwardly directly protrusion configured to interact into the paths on the outer surface of the rotator member, such that when proximal generally tubular part is pressed against a drug delivery site, the actuation member is linearly and distally displaced thereby forcing the rotator member to rotate from the locked position to the released position.

6. The medicament delivery device of claim 5, further comprising a security locking member extending through a distal end of the housing and having a proximal end operatively connected to the actuation member, wherein the security locking member is movable between a first position, in which the security locking member is locked to the actuation member for preventing linear and distal displacement of the actuation member when the actuation member is pressed against the drug delivery site, and a second position, in which the security locking member is unlocked from the actuation member for allowing linear and distal displacement of the actuation member when the actuation member is pressed against the drug delivery site.

7. The medicament delivery device of claim 1, wherein the device is a disposable auto-injection device.

8. The medicament delivery device of claim 1, wherein the dual back-to-back force spring assembly includes two springs each of strip material having a front side surface and a back side surface and pre-tensioned into a tightly wound roll with an outer end, each roll is cradled in a corresponding seat of the hold member, and each outer end has its back side surface toward the other outer end and attached to a respective side of a transversal post attached to a distal end of the plunger rod.

9. The medicament delivery device of claim 1, wherein the device is a disposable auto-injection device.

10. A medicament delivery device, comprising:
    a housing configured for a medicament container;
    a drive unit in the housing and configured for acting on a movable stopper in the medicament container for expelling a dose of medicament, wherein the drive unit includes an elongated plunger rod and a dual back-to-back force spring assembly operatively connected to the plunger rod so as to provide a symmetrical load on the plunger rod; and
    a lock and release mechanism operatively connected to the drive unit and configured for releasing the drive unit upon activation, wherein the lock and release mechanism includes a hold member operatively connected to the plunger rod, a rotator member operatively connected to the hold member, and a tubular actuation member linearly slidable in relation to the housing and operatively connected to the rotator member;
    wherein the hold member is fixedly attached to the housing and includes a generally tubular lock tube through which the plunger rod extends and two half-cylindrical seats open toward a proximal direction for housing the dual back-to-back force spring assembly; the lock tube includes a resilient lock and release device configured to interact with both the plunger rod and the rotator member; the dual back-to-back force spring assembly includes two springs each of strip material having a front side surface and a back side surface and pre-tensioned into a tightly wound roll with an outer end; each roll is cradled in a corresponding seat of the hold member; each outer end has its back side surface toward the other outer end and attached to a respective side of a transversal post attached to a distal end of the plunger rod; and the resilient lock and release device includes two oppositely positioned radial flexible tongues, each with a first radial inwardly directed protrusion and with a first radial outwardly directed protrusion.

11. The medicament delivery device of claim 10, wherein the plunger rod and spring assembly are movable between a loaded state, in which a proximal end of the plunger rod abuts the stopper positioned at a distal end in the medicament container and in which a portion of the strip material is unrolled and extends parallel on each side of the plunger rod, and a relaxed state, in which the plunger rod abuts the stopper positioned at a proximal end in the medicament container and in which the strip material is rolled up.

12. The medicament delivery device of claim 11, wherein the rotator member has an inner circumferential surface having inner ledges and inner grooves and an outer circumferential surface having a number of outer guides in two paths on opposite sides of the rotator member.

13. The medicament delivery device of claim 12, wherein the rotator member rotates between a locked position, in which the first radial outwardly directed protrusions interact with the ledges thereby forcing the radial flexible tongues radially inward such that the first radial inwardly directed protrusions engage into the recesses of the plunger rod for holding the plunger rod and spring assembly in the loaded state, and a released position, in which the first radial outwardly directed protrusions interact with the inner grooves on the inner surface of the rotator member thereby forcing the radial flexible tongues radially outward such that the first radial inwardly directed protrusions disengage from the recesses of the plunger rod for releasing the plunger rod and the spring assembly from the loaded state.

14. The medicament delivery device of claim 13, wherein the tubular actuation member comprises a proximal generally tubular part protruding through the proximal end of the housing, and two longitudinally extending arms; each longitudinally extending arm comprises a second radial inwardly directly protrusion configured to interact into the paths on the outer surface of the rotator member, such that when proximal generally tubular part is pressed against a drug delivery site, the actuation member is linearly and distally displaced thereby forcing the rotator member to rotate from the locked position to the released position.

15. The medicament delivery device of claim 14, further comprising a security locking member extending through a distal end of the housing and having a proximal end operatively connected to the actuation member, wherein the security locking member is movable between a first position, in which the security locking member is locked to the actuation member for preventing linear and distal displacement of the actuation member when the actuation member is pressed against the drug delivery site, and a second position, in which the security locking member is unlocked from the actuation member for allowing linear and distal displacement of the actuation member when the actuation member is pressed against the drug delivery site.

* * * * *